US012738348B2

(12) United States Patent
Hirono et al.

(10) Patent No.: US 12,738,348 B2
(45) Date of Patent: Sep. 15, 2026

(54) OPTICAL INFORMATION READING APPARATUS AND METHOD

(71) Applicant: OPTOELECTRONICS CO., LTD., Warabi (JP)

(72) Inventors: Mitsuaki Hirono, Saitama (JP); Shuji Noda, Saitama (JP); Nobutake Fusayasu, Saitama (JP); Takashi Sampei, Saitama (JP)

(73) Assignee: OPTOELECTRONICS CO., LTD, Saitama (JP)

( * ) Notice: Subject to any disclaimer, the term of this patent is extended or adjusted under 35 U.S.C. 154(b) by 0 days.

(21) Appl. No.: 19/034,642

(22) Filed: Jan. 23, 2025

(65) Prior Publication Data

US 2026/0074034 A1 Mar. 12, 2026

(30) Foreign Application Priority Data

Sep. 10, 2024 (JP) ................................ 2024-156600

(51) Int. Cl.

*G16H 10/40* (2018.01)
*G06K 7/14* (2006.01)
*G06K 19/06* (2006.01)

(52) U.S. Cl.

CPC ........... *G16H 10/40* (2018.01); *G06K 7/1417* (2013.01); *G06K 19/06037* (2013.01)

(58) Field of Classification Search

None
See application file for complete search history.

(56) References Cited

U.S. PATENT DOCUMENTS

| | | | |
|---|---|---|---|
| 9,547,784 B1 | 1/2017 | Montag et al. | |
| 2002/0134923 A1 | 9/2002 | Watari | |
| 2009/0032403 A1 | 2/2009 | Malhotra | |
| 2009/0324032 A1 * | 12/2009 | Chen ..................... | G06T 7/0008 382/128 |
| 2019/0041318 A1 | 2/2019 | Wissmann et al. | |
| 2019/0271714 A1 | 9/2019 | Kluckner | |
| 2020/0103425 A1 | 4/2020 | Inagaki | |
| 2023/0079568 A1 | 3/2023 | Baba | |

FOREIGN PATENT DOCUMENTS

| | | |
|---|---|---|
| DE | 19745813 | 4/1999 |
| JP | 2002-286424 | 10/2002 |
| JP | 2007-279950 | 10/2007 |
| JP | 2020-052021 | 4/2020 |
| WO | 2018/022280 | 2/2018 |
| WO | 2021/182038 | 9/2021 |

OTHER PUBLICATIONS

Extended European Search Report for European Patent Application No. 25154778.2 dated Jun. 30, 2025.

* cited by examiner

*Primary Examiner* — Kristy A Haupt
(74) *Attorney, Agent, or Firm* — Amin, Turocy & Watson, LLP

(57) ABSTRACT

An apparatus that detects a cap attached to a container containing a specimen or a reagent, and includes: an imager that acquires an image of the container together with a pattern arranged in a background of the container; and a controller that decodes from the image a code attached to the container. The controller recognizes specific classified results including the pattern from the image, and detects the cap based on presence or absence of the specific classified results.

6 Claims, 12 Drawing Sheets

OPTICAL INFORMATION READING APPARATUS AND METHOD

CROSS REFERENCE TO RELATED APPLICATIONS

This application is entitled to (or claims) the benefit of Japanese Patent Application No. 2024-156600, filed on Sep. 10, 2024, the disclosure of which including the specification, drawings and abstract is incorporated herein by reference in its entirety.

TECHNICAL FIELD

The present disclosure relates to an optical information reading apparatus and method.

BACKGROUND ART

Test tubes or reagent bottles containing specimens used in specimen testing apparatuses (biochemical automatic analysis apparatus) such as blood testing apparatuses are usually capped to prevent the contents from leaking during transportation. The specimen testing apparatus includes a tub-shaped container, and the operator sets a test tube or a reagent bottle with the cap removed into this tub-shaped container to perform a biochemical test using the specimen testing apparatus.

The specimen testing apparatus sequentially suctions liquid from the test tube or the reagent bottle with a probe (suction tube) provided at the tip of a dispenser, dispenses the liquid into a mixing reaction container, and causes a specimen and a reagent to react with each other to perform the biochemical test.

Since the probe (suction tube) is configured in the form of a thin metal pipette, the probe is easily broken or bent. In this case, if the operator sets a test tube or a reagent bottle without removing the cap, the probe may be damaged by hitting the cap.

In order to solve such a problem, techniques for detecting the presence or absence of a cap of a test tube (specimen container or reagent bottle) through image recognition are known in PTL 1 and 2.

U.S. Patent Application Publication No. 2009/0324032 (hereinafter referred to as PTL 1) discloses a system in which a test tube and a cap are identified. In a sub-process of tube identification, an image captured by an optical imager is used, and the features of the test tube and the cap shape are extracted and the cap detection of the test tube is performed by using contrast in a retroreflective target region with highly brightened background.

International Publication No. 2018/022280 (hereinafter referred to as PTL 2) discloses a system for identifying a cap of a specimen container. A specimen container including a cap is imaged through irradiation with light sources of different wavelengths for a plurality of exposure times. From a plurality of captured images, pixels with appropriate exposure for each wavelength are selected, and the pixels in the image are classified as belonging to each region such as the transparent portion of the test tube, the cap, the label, and the like. From the classified data, the shape, capacity, characteristics, and the like are identified for each region, and the size of the test tube, the type of cap, the color of the cap, and the like are identified.

Further, International Publication No. 2021/182038 (hereinafter referred to as PTL 3) describes an automatic analysis apparatus that detects a specimen container even if a barcode label is not attached to the specimen container. A two-dimensional code is disposed at the back surface position of the mounting section of the specimen container, and the two-dimensional code is read by sensor 16. Whether a specimen container is mounted on the mounting section is determined based on whether the contrast value of light reflected from the two-dimensional code portion is equal to or greater than a preset threshold.

Further, Japanese Patent Application Laid-Open No. 2007-279950 (hereinafter referred to as PTL 4) discloses an optical information reading apparatus for appropriately reading a two-dimensional code displayed on a mobile phone using a background plate with a pattern. A mobile phone inserted between the background plate and the sensor is captured by the light-receiving sensor. From the image of the light-receiving sensor, the change in a black-and-white output signal for each coordinate is detected, and the position and movement speed of the mobile phone are detected. The imaging conditions for reading the two-dimensional code are set based on the detected position and movement speed of the mobile phone.

SUMMARY OF INVENTION

Technical Problem

The above-described conventional detection methods have the following problems.

In PTL 1, the retroreflective target region is fixed, which limits the position of the cap that can be discriminated, and consequently various heights of specimen containers cannot be detected.

In PTL 2, a multi-wavelength light source is used, and therefore a high-performance sensor is required for cap detection and the identification processing is complicated. Additionally, if the cap or label has the same wavelength (color) as the light source, it cannot be discriminated.

In PTL 3, the presence or absence of a specimen container is detected with a sensor by utilizing a transmission portion of the specimen container, but the automatic analysis apparatus does not take into account the detection of a cap.

PTL 4 discloses a technique for obtaining coordinates from a pattern in the background, but it does not contribute to a technique for detecting a cap of a specimen container.

There are specimen containers with various heights and thicknesses, and it is desirable that all types can be handled in identification using images. Further, the caps of the specimen containers may have various colors including bright colors to dark colors such as white, brown, and purple, and it is desirable that detection of the cap can be made regardless of the color of the cap.

An object of the present invention is to provide an optical information reading apparatus, method, and program that detect caps of test tubes (specimen containers or reagent bottles) of various sizes more easily and reliably, and a non-limiting embodiment of the present disclosure contributes to providing an optical information reading apparatus, method, and program that identify caps of test tubes (specimen containers or reagent bottles) of various sizes with high accuracy and easily.

Solution to Problem

An optical information reading apparatus according to an embodiment of the present disclosure includes: an imager that acquires an image by imaging a container to which a code is attached and a pattern arranged in a background of the container; and a controller that decodes the code from the image and detects presence or absence of a cap of the container based on a state of the pattern in the image.

An optical information reading method according to an embodiment of the present disclosure includes: by an optical information reading apparatus, acquiring an image by imaging a container to which a code is attached and a pattern arranged in a background of the container; and decoding the code from the image, and detecting presence or absence of a cap of the container based on a state of the pattern in the image.

An optical information reading program according to an embodiment of the present disclosure includes causes an optical information reading apparatus to execute: acquiring an image by imaging a container to which a code is attached and a pattern arranged in a background of the container; and decoding the code from the image, and detecting presence or absence of a cap of the container based on a state of the pattern in the image.

These comprehensive or specific aspects may be realized in a system, device, method, integrated circuit, computer program, or recording medium, or in any combination of a system, device, method, integrated circuit, computer program, and recording medium.

Advantageous Effects of Invention

According to the optical information reading apparatus of the present disclosure, it is possible to effectively prevent damage to a probe (suction tube) by detecting and notifying a user of a failure to remove the cap from a test tube (specimen container, reagent bottle). Further, according to the optical information reading apparatus of the present disclosure, by using a background label with a pattern including a certain repeating pattern, it is possible to facilitate discrimination through image recognition and to greatly improve the accuracy of the discrimination, and thus, it is possible to detect a failure to remove the cap of the test tube more easily and with higher accuracy.

Further advantages and effects of an embodiment of the present disclosure will be apparent from the specification and drawings. Such advantages and/or effects are provided by some embodiments and features described in the specification and drawings, respectively, but not necessarily all in order to obtain one or more identical features.

DESCRIPTION OF EMBODIMENTS

Figure 1:
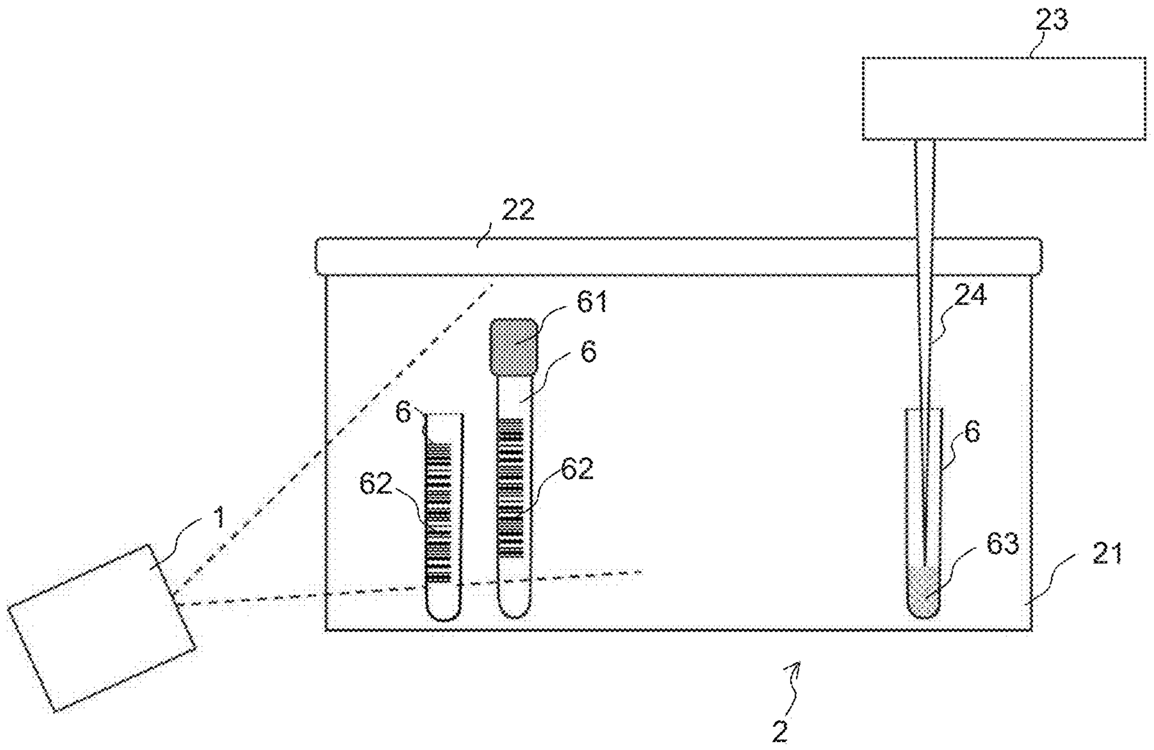
FIG. 1 is a diagram illustrating an example of a specimen testing apparatus in which an optical information reading apparatus according to an embodiment of the present disclosure is installed.

The following is a detailed description of the embodiment of the present disclosure, referring to the drawings as appropriate. However, more detailed explanations than necessary may be omitted. For example, detailed explanations of matters already well known or duplicate explanations for substantially identical configurations may be omitted. This is to avoid unnecessary redundancy in the following explanations and to facilitate the understanding of those skilled in the art.

The accompanying drawings and the following description are provided to enable those skilled in the art to fully understand the disclosure, and are not intended to limit the subject matter recited in the claims. The embodiments described below are examples, and the embodiments to which this disclosure applies are not limited to those described below.

EMBODIMENT

Configuration of Specimen Testing Apparatus

Figure 2:
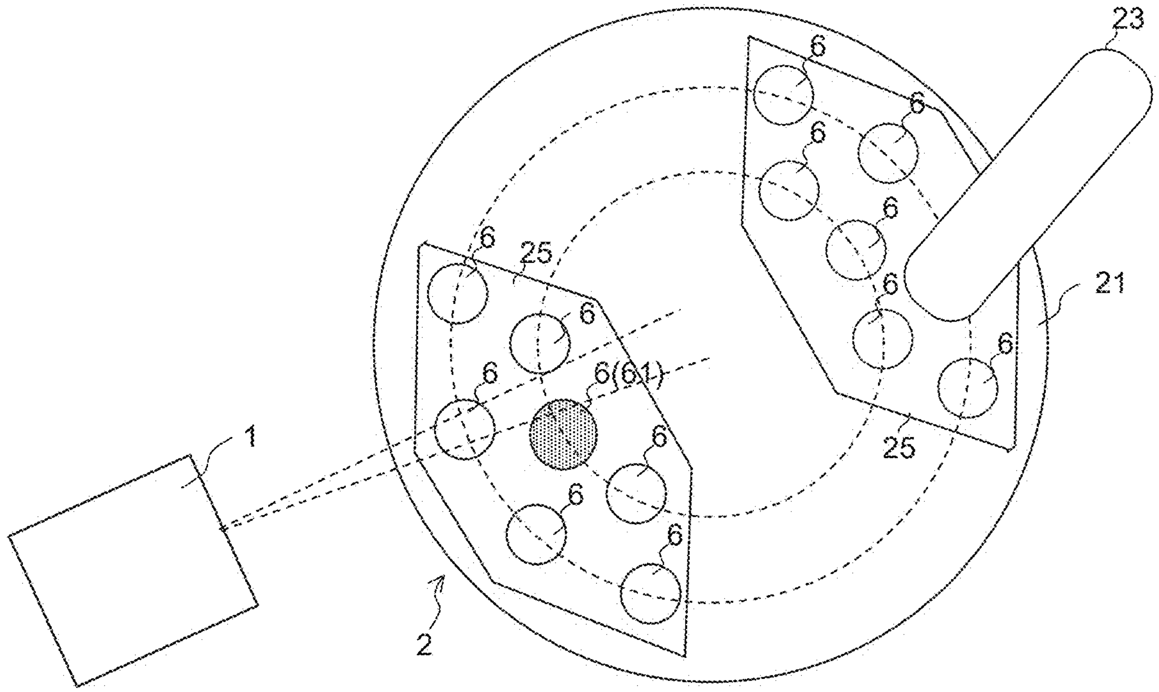
FIG. 2 is a diagram illustrating an example of the specimen testing apparatus in which the optical information reading apparatus according to the embodiment of the present disclosure is installed.

FIGS. 1 and 2 are examples of a medical specimen testing apparatus 2 (biochemical automatic analysis apparatus) in which optical information reading apparatus 1 according to an embodiment of the present disclosure is installed. Specimen testing apparatus 2 is installed such that tub-shaped turntable container 21 rotates. In order to maintain the quality of specimen 63, the tub-shaped turntable container 21 is provided with a cooling function, and lid 22 is provided in an attachable manner for cold storage.

Tub-shaped turntable container 21 is provided with rack 25, and rack 25 is configured such that a plurality of holders are provided in the circumferential direction and a plurality of test tubes 6 (specimen containers or reagent bottles) are attached. Further, a label on which barcode 62 or a two-dimensional code for identifying the specimen or the reagent accommodated in test tube 6 is printed is attached to test tube 6. Further, a slit or a window is provided in tub-shaped turntable container 21 and rack 25, and optical information reading apparatus 1 is configured to be capable of capturing test tube 6 and a label attached to test tube 6 from the outside of tub-shaped turntable container 21.

The operator sets test tube 6, from which cap 61 has been removed, in the holder of rack 25 of tub-shaped turntable container 21, and performs a biochemical test with specimen testing apparatus 2. When specimen testing apparatus 2 is activated, specimen testing apparatus 2 sequentially suctions from test tube 6 sample 63 and a reagent corresponding to the testing item with probe (suction tube) 24 provided at the distal end of dispenser 23, and dispenses them into a mixing reaction container so as to cause reaction between sample 63 and the reagent. Subsequently, specimen testing apparatus 2 performs a biochemical test by measuring the absorbance, turbidity, or the like of the reaction product with a photometer and quantifying the target component in sample 63.

Functions of Optical Information Reading Apparatus

As illustrated in FIGS. 1 and 2, optical information reading apparatus 1 is a 2D imager installed in specimen testing apparatus 2. As described below, optical information reading apparatus 1 has functions of (1) a barcode reader and (2) a cap-removal failure detection.

Optical information reading apparatus 1 sequentially acquires images of test tubes 6, each set in a holder of rack 25 of tub-shaped turntable container 21, reads barcode 62 or two-dimensional code which are attached to test tubes 6, and decodes the content of barcode 62 or two-dimensional code. Optical information reading apparatus 1 transfers to specimen testing apparatus 2 the decoded content of read barcode 62 or two-dimensional code of test tube 6. Specimen testing apparatus 2 identifies specimen 63 to be tested from the received content of barcode 62 or two-dimensional code of test tube 6.

As described above, if the operator sets test tube 6 in the holder of rack 25 of tub-shaped turntable container 21 without removing cap 61, probe (suction tube) 24 may come into contact with cap 61, causing probe (suction tube) 24 to break or bend.

In order to detect the failure to remove cap 61, which is the cause of damage to probe 24 and to notify the operator, optical information reading apparatus 1 recognizes the acquired image of test tube 6 and detects the presence or absence of cap 61 on test tube 6. When optical information reading apparatus 1 detects cap 61 of test tube 6, optical information reading apparatus 1 transfers the information of the cap detection to specimen testing apparatus 2 and notifies the operator using a buzzer, an LED indicator, or the like. From the notification, the operator can notice the failure to remove cap 61 of test tube 6. Further, specimen testing apparatus 2 may be configured to stop the biochemical testing when specimen testing apparatus 2 receives information on cap detection.

Optical Information Reading Apparatus

Figure 3:
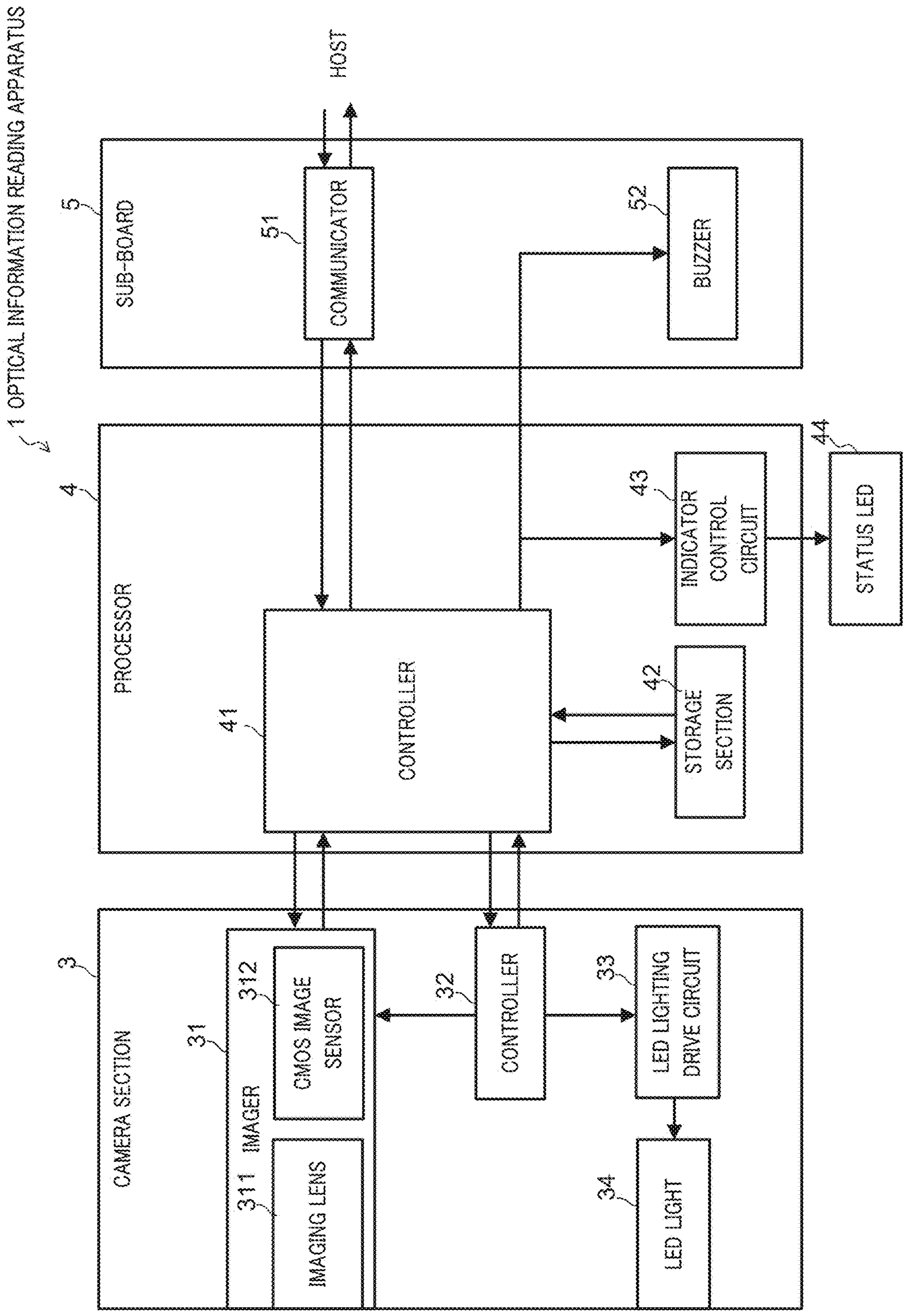
FIG. 3 is a block diagram illustrating an exemplary configuration of the optical information reading apparatus according to the embodiment of the present disclosure.

FIG. 3 is a block diagram illustrating an example of optical information reading apparatus 1. Optical information reading apparatus 1 is configured with camera section 3, processor 4, and sub-board 5. This configuration is described below.

Camera Section

Camera section 3 includes imager 31, controller 32, LED lighting drive circuit 33, and LED light 34.

Imager 31 includes imaging lens 311 and complementary metal oxide semiconductor (CMOS) image sensor 312. CMOS image sensor 312 may be a grayscale CMOS image sensor or a color CMOS image sensor. Imaging lens 311 of imager 31 is, for example, an optical lens, and forms an image of an object on the optical axis on the imaging area of CMOS image sensor 312. Thus, CMOS image sensor 312 can acquire image data of the imaging target object.

Controller 32 is a general-purpose microprocessor, and controls camera section 3 in general by controlling imager 31 of camera section 3 and LED lighting drive circuit 33 that drives LED light 34. Controller 32 may be realized by, for example, a microcontroller unit (MCU) in which peripheral functions such as a central processing unit (CPU) and a storage section (memory) are integrated into one.

LED lighting drive circuit 33 is a circuit that drives LED light 34 for illuminating the imaging target.

LED light 34 emits light to the object to illuminate the object. Thus, imager 31 can capture clear image data even in enclosed, dark places.

Processor

Processor 4 includes controller 41, storage section 42, indicator control circuit 43, and status LED 44.

Controller 41 is a processor that controls the overall operation of optical information reading apparatus 1. Controller 41 may be realized by, for example, a central processing unit (CPU) or the like.

Controller 41 operates as a barcode reader by loading from storage section 42 software that has a function of reading and decoding barcode 62. Controller 41 reads barcode 62 from the image data acquired by camera section 3, discriminates the code system, and decodes the data of barcode 62.

Further, controller 41 also functions as a functional section that detects the failure to remove cap 61 through image recognition by reading from storage section 42 software that has a function of detecting the failure to remove cap 61 through image recognition. Details of this processing will be described later with a flowchart of the detection processing using image recognition.

Storage section 42 is configured with a main storage section including a memory such as a DRAM (Dynamic Random Access Memory) for storing data and instructions read by controller 41, and an auxiliary storage section including a flash memory or the like capable of stably holding information such as a program even in a power-off state. By the program stored in storage section 42, controller 41 operates as a functional section that activates software to realize each function. Further, storage section 42 stores image data input from camera section 3, data necessary for the operations of the image recognition processing and the detection processing, and the like.

Indicator control circuit 43 is a control circuit for driving the LED of status LED 44 as an indicator in accordance with the operation state of optical information reading apparatus 1 or the detection result of the image data acquired by camera section 3. For example, when a failure to remove cap 61 of test tube 6 is detected from the image acquired by camera section 3, indicator control circuit 43 turns on status LED 44 in a predetermined manner.

Status LED 44 is composed of a plurality of LEDs and is an LED for notifying an operator or the like of the operation state of optical information reading apparatus 1 or the detection result of image recognition (such as a failure to remove cap 61) for the image data acquired by camera section 3.

Sub-Board

Sub-board 5 includes communicator 51 and buzzer 52.

Communicator 51 is connected to specimen testing apparatus 2 (host) in a communicative manner via RS-232C, USB, or the like.

Buzzer 52 notifies the operator or the like of the operation state of optical information reading apparatus 1 and the detection result of image recognition acquired by camera section 3 (such as a failure to remove cap 61) by outputting a notification sound.

Image Acquisition by Optical Information Reading Apparatus

Optical information reading apparatus 1 is installed in specimen testing apparatus 2 with the optical axis of imaging lens 311 directed upward, and acquires images of each test tube 6 set in the holder of rack 25 in tub-shaped turntable container 21 of specimen testing apparatus 2 (see FIGS. 4 to 7). Each test tube 6 set in the holder is imaged one by one by optical information reading apparatus 1, and vertically long images that are visible through the gap in the holder are acquired (see FIGS. 9A to 9I).

Background Label

Figure 4:
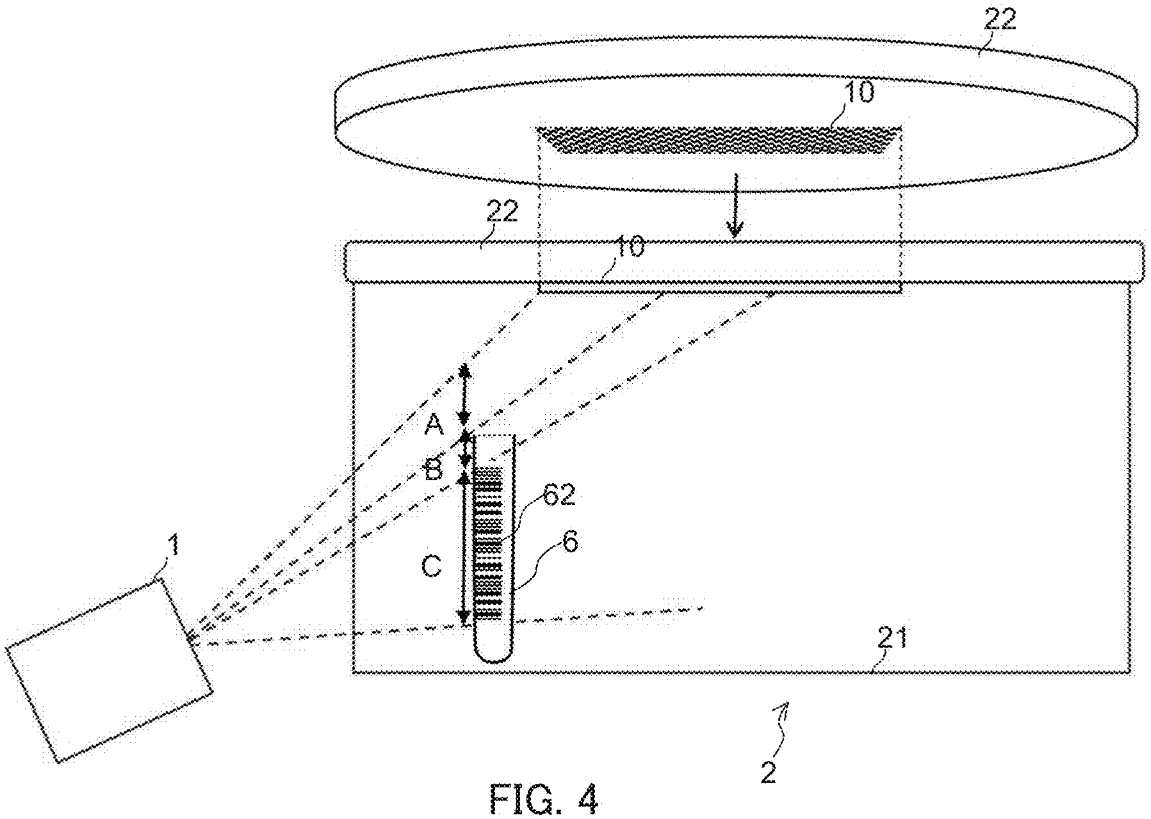
FIG. 4 is a diagram illustrating an example of imaging of a test tube using a background label by the optical information reading apparatus according to the embodiment of the present disclosure.

In installation of optical information reading apparatus 1, the installation person attaches background label 10 to the back surface of lid 22 of tub-shaped turntable container 21 (see FIG. 4). With background label 10, when optical information reading apparatus 1 images each test tube 6 at an elevation angle, the pattern of background label 10 attached to lid 22 is imaged in the background of the captured image. Background label 10 is, for example, a label on which a checkerboard pattern as illustrated in FIG. 8A is printed. Background label 10 is used to improve the accuracy of detection processing using image recognition and to facilitate image recognition.

Next, the following describes variations in imaging for a case where cap 61 is not mounted on test tube 6 and a case where cap 61 is mounted on test tube 6 on the basis of the examples illustrated in FIGS. 4 to 7.

Case Where Cap is Not Mounted on Test Tube

Figure 5:
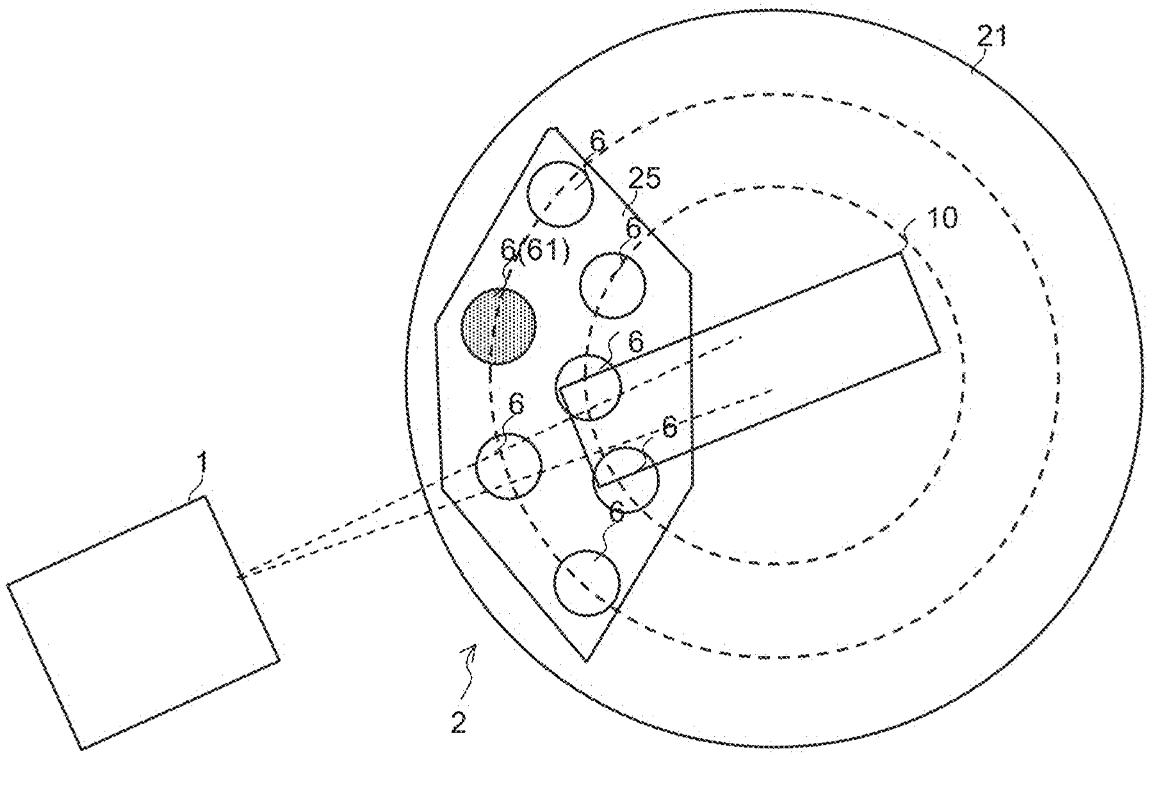
FIG. 5 is a diagram illustrating an example of imaging of a test tube using a background label by the optical information reading apparatus according to the embodiment of the present disclosure.

FIGS. 4 and 5 are diagrams illustrating an example of imaging of test tube 6 by optical information reading apparatus 1 in a case where cap 61 is not mounted on test tube 6.

Figure 10A:
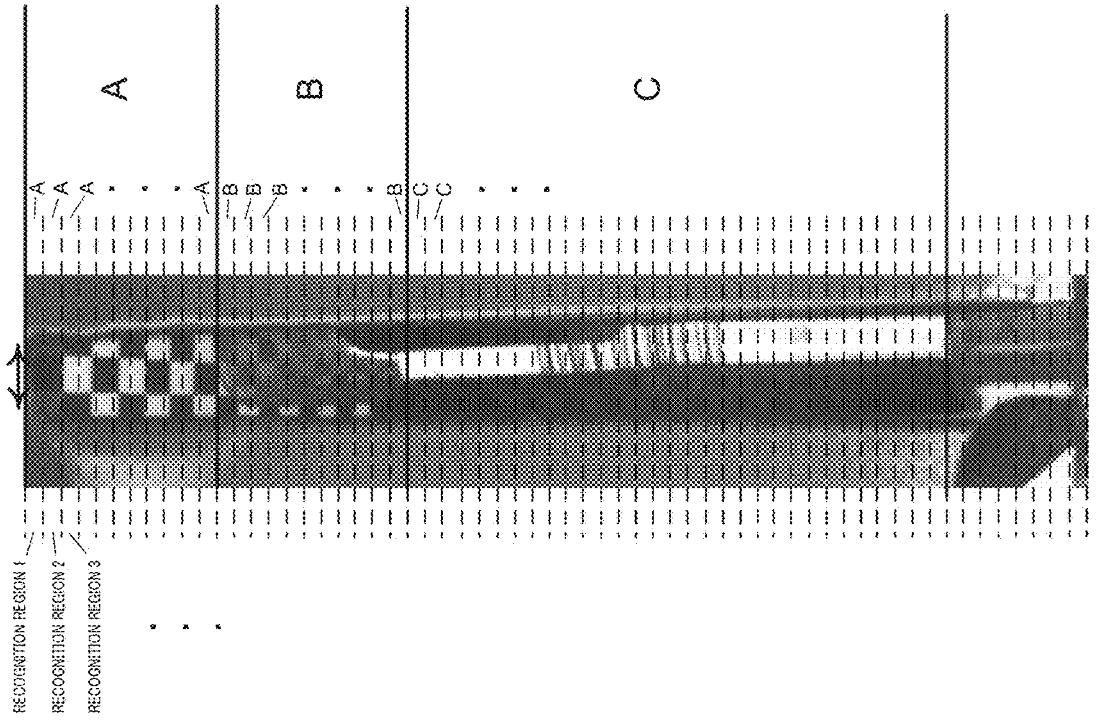
FIGS. 10A to 10C are diagrams illustrating an example of a recognition region of a captured image and recognized results obtained by the optical information reading apparatus according to the embodiment of the present disclosure.
Figure 11:
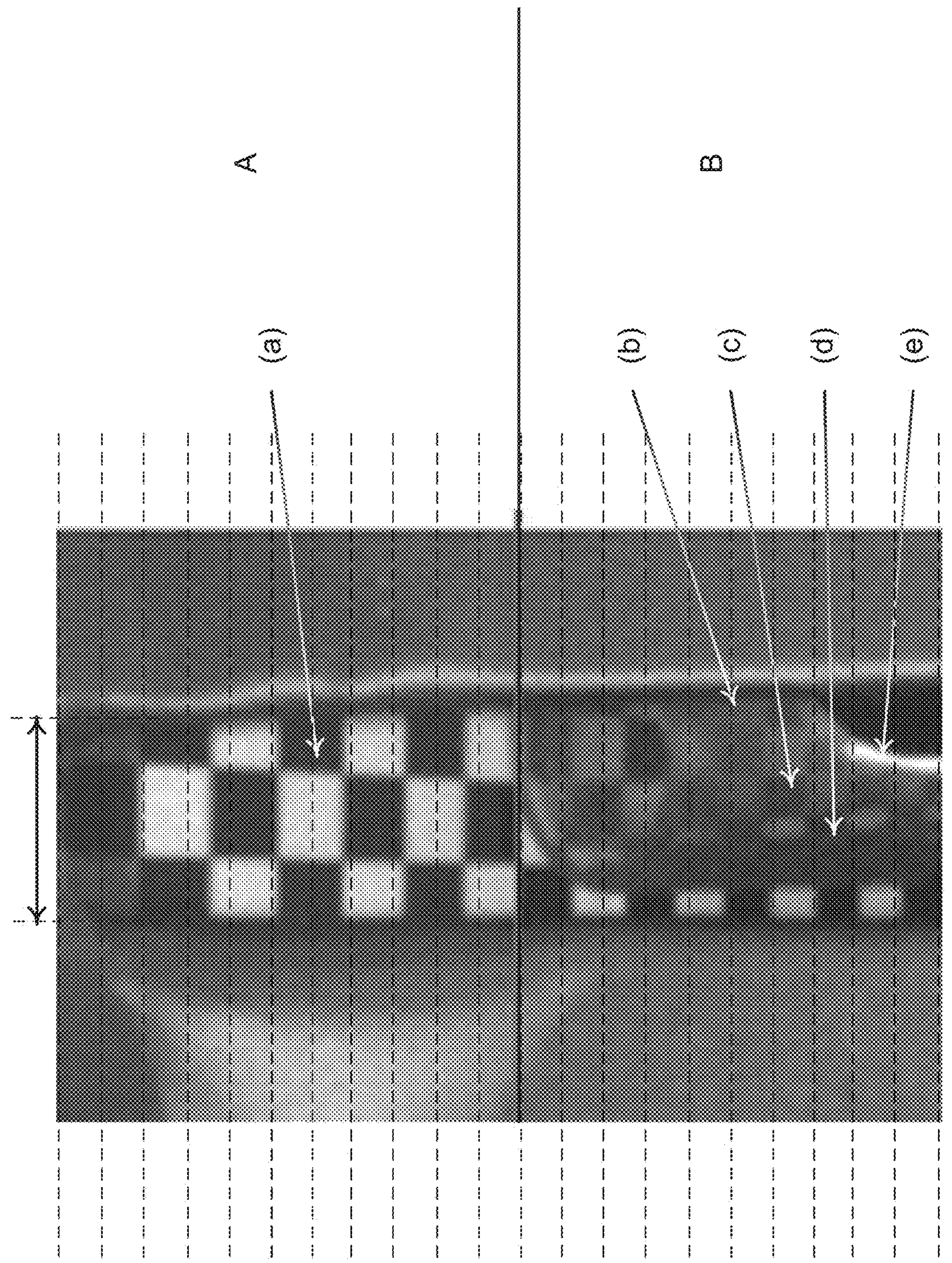
FIG. 11 is a diagram illustrating an example of a recognition region of a captured image and recognized results (A and B) obtained by the optical information reading apparatus according to the embodiment of the present disclosure.

The range indicated by A in FIG. 4 is an upper side of test tube 6, and is a range in which background label 10 is imaged in a state with no obstruction (see A in FIG. 10A and (a) of a part A in FIG. 11). In background label 10, a pattern including a certain repeating pattern is imaged clearly.

Next, the range indicated by B in FIG. 4 is a range in which background label 10 is imaged through test tube 6 (see B in FIG. 10A and B in FIG. 11). In the range indicated by B, the light that has passed through the transparent glass or plastic of test tube 6 is bent and refracted, resulting in the pattern including the certain repeating pattern of background label 10 imaged in a distorted state (see (c) of B in FIG. 11), the pattern including the certain repeating pattern of background label 10 imaged with a reduced contrast (see (b) of B in FIG. 11), or the pattern including the certain repeating pattern of background label 10 imaged in a state of being hidden by the refracted light or the reflected light (see (d) and (e) of B in FIG. 11).

The range indicated by C in FIG. 4 below is a range in which the label of barcode 62 attached to test tube 6 is imaged (see C in FIG. 10A). In other words, the range indicated by C is a range in which a pattern including a certain repeating pattern of background label 10 is imaged in a state of being completely blocked by a smooth label surface on which barcode 62 or characters are printed.

When test tube 6 is imaged by optical information reading apparatus 1 as illustrated in FIGS. 4 and 5, the image is captured as illustrated in FIG. 9B, 9D, 9F, or 9H. FIGS. 9B and 9D, and 9F and 9H differ from one another in the size of the test tubes. FIG. 10A is the same image as FIG. 9D.

Case Where Cap is Mounted on Test Tube

Figure 6:
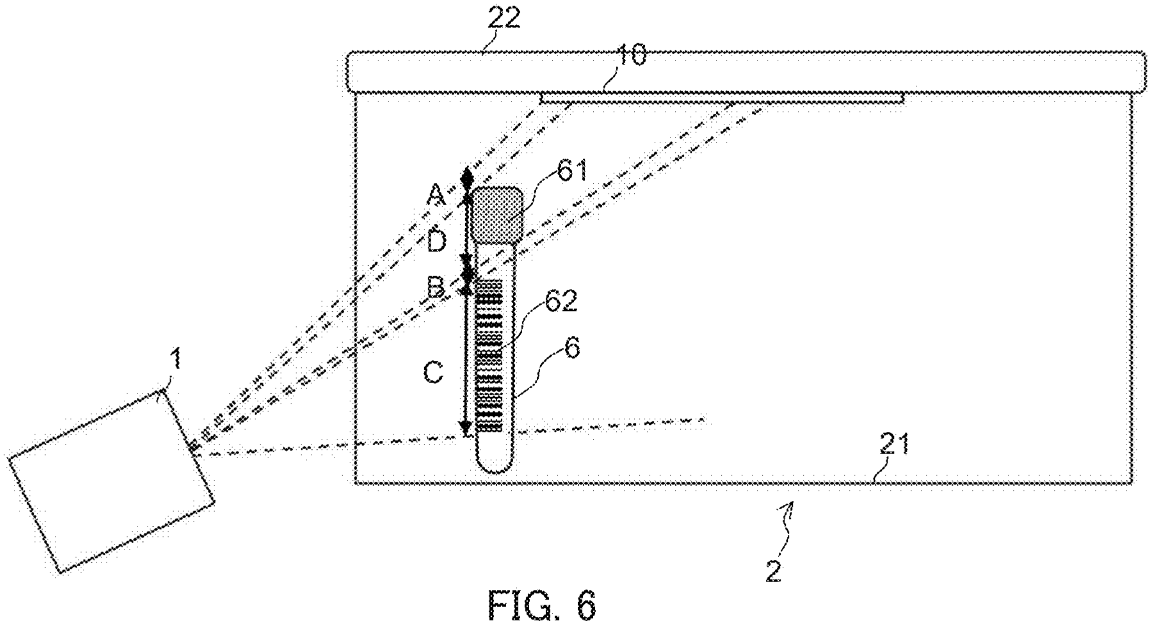
FIG. 6 is a diagram illustrating an example of imaging of a test tube using a background label by the optical information reading apparatus according to the embodiment of the present disclosure.
Figure 7:
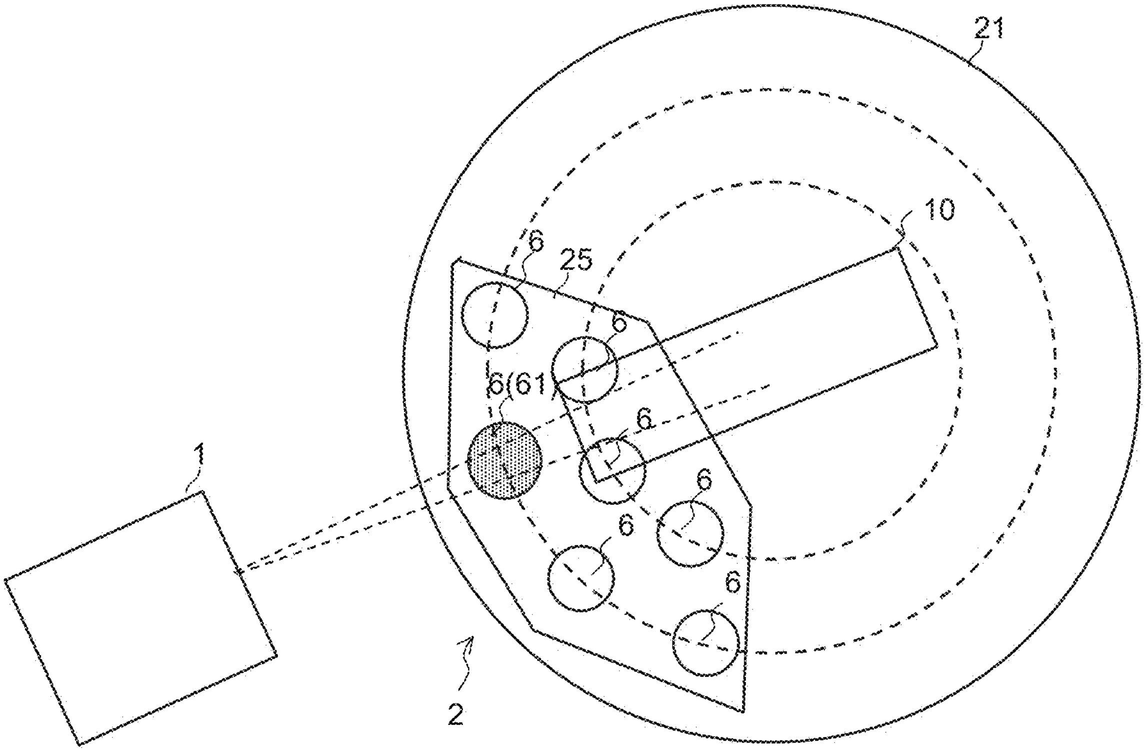
FIG. 7 is a diagram illustrating an example of imaging of a test tube using a background label by the optical information reading apparatus according to the embodiment of the present disclosure.

FIGS. 6 and 7 are diagrams illustrating an example of imaging of a test tube by optical information reading apparatus 1 in a case where cap 61 is mounted on test tube 6.

Figure 10B:
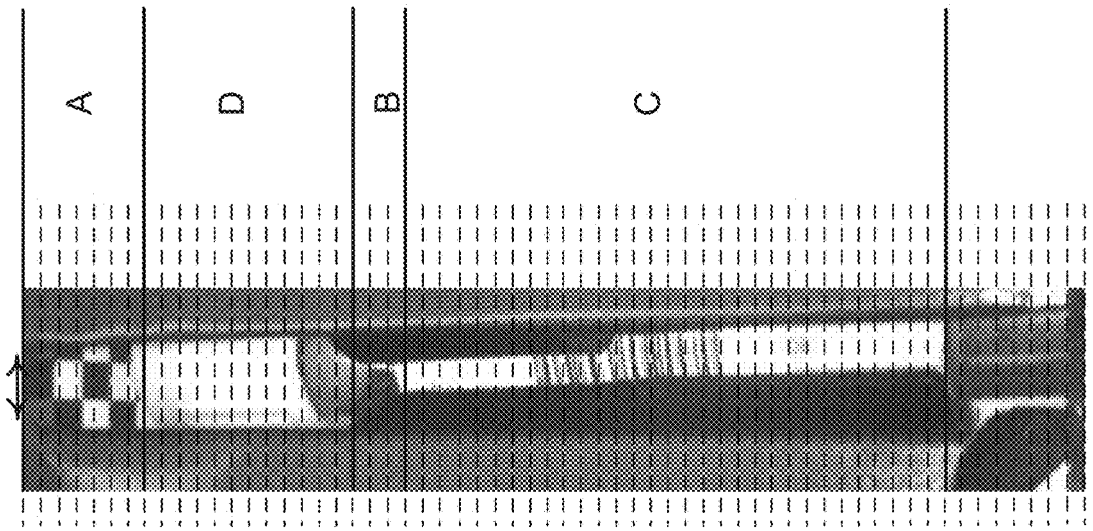

The range indicated by A in FIG. 6 is a range in which background label 10 is imaged in a state with no obstruction (see A in FIG. 10B).

Next, the range indicated by D in FIG. 6 is a range in which cap 61 mounted on test tube 6 is imaged (see D in FIG. 10B). It can be seen that a groove or a surface for preventing slipping is processed in the gripping portion of cap 61. In other words, the range indicated by D is a range in which a pattern including a certain repeating pattern of background label 10 is imaged in a state of being completely blocked by cap 61.

The range indicated by B in FIG. 6 below the range indicated by D is a range in which background label 10 is imaged through test tube 6 (see B in FIG. 10B).

Further, the range indicated by C in FIG. 6 is a range in which the label of barcode 62 attached to test tube 6 is imaged but background label 10 is not imaged (see C in FIG. 10B).

In a case where test tube 6 is imaged by optical information reading apparatus 1 as illustrated in FIGS. 6 and 7, test tube 6 is imaged as an image illustrated in FIG. 9C, 9E, 9G, or 9I. FIGS. 9C and 9E, and 9G and 9I differ from one another in the size of the test tubes. Note that FIG. 10B is the same image as FIG. 9E.

Case Where Test Tube is Not Set

Figure 9I:
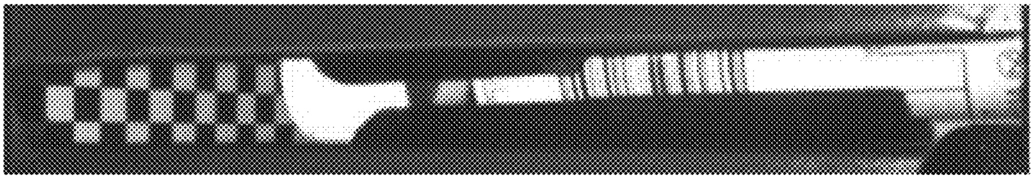
FIGS. 9A to 9I are diagrams illustrating an example of a captured image by the optical information reading apparatus according to the embodiment of the present disclosure.
Figure 9H:
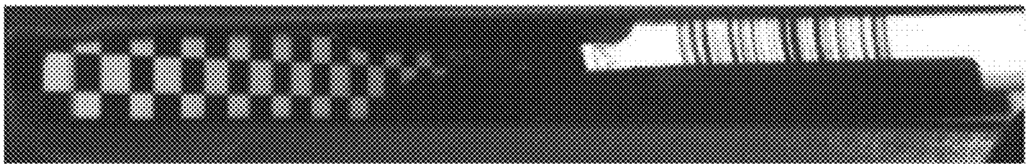
Figure 9G:
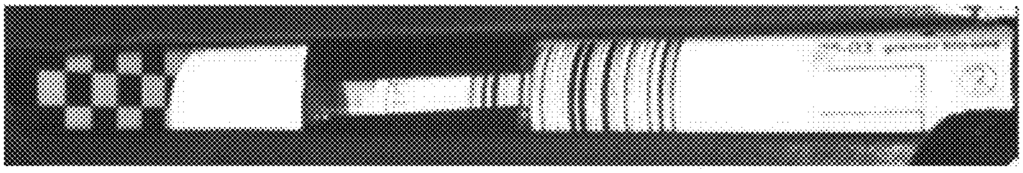
Figure 9F:
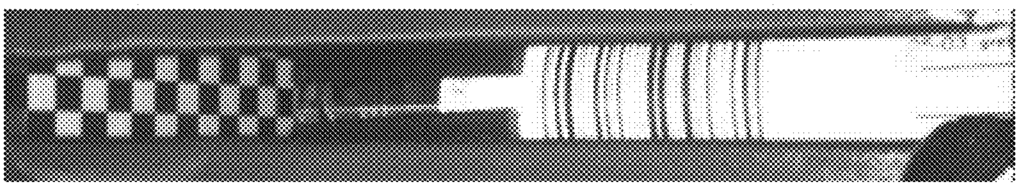
Figure 9E:
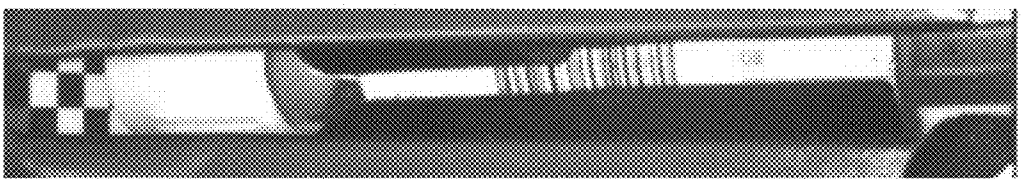
Figure 9D:
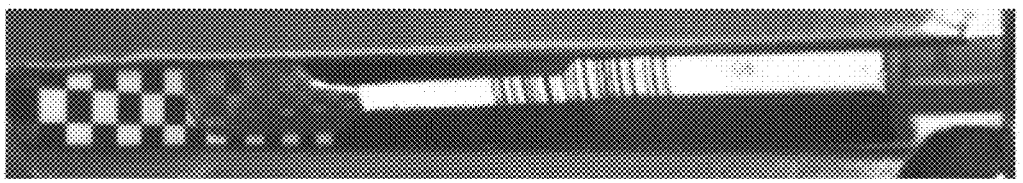
Figure 9C:
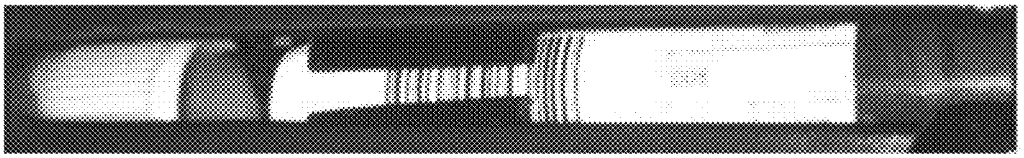
Figure 9B:
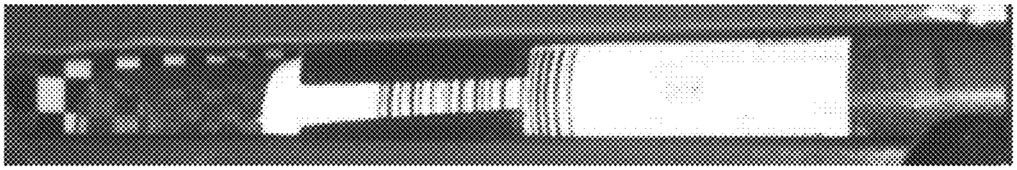
Figure 9A:
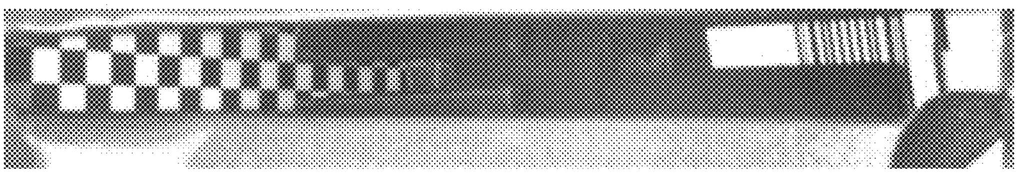
Figure 10C:
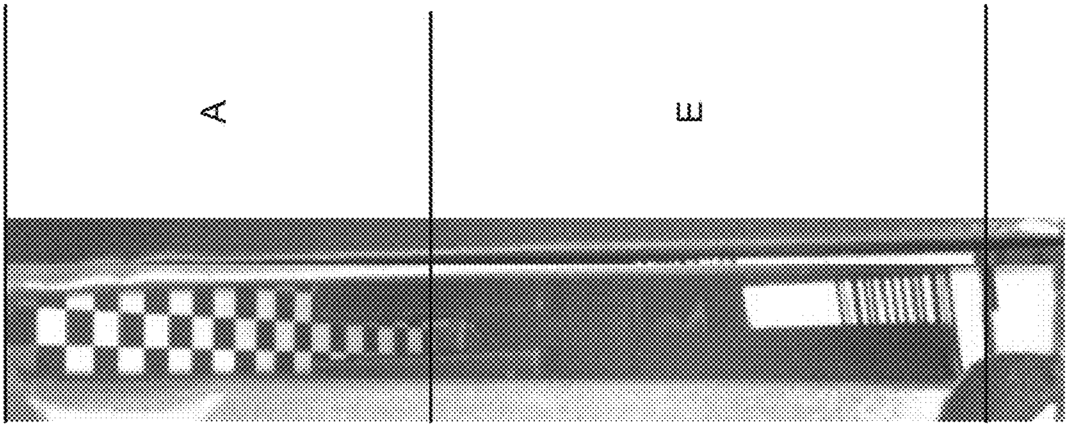

In a case where test tube 6 is not set in the holder of rack 25, the image captured by optical information reading apparatus 1 is captured as illustrated in FIG. 9A or FIG. 10C. The following ranges are included: the range in which background label 10 is imaged with no obstacle from the upper portion (see A in FIG. 10C), the range in which the inner surface of rack 25 is imaged as a dark space (see the upper side of E in FIG. 10C), and the range in which a small barcode is imaged (see the lower side of E in FIG. 10C). Note that the small barcode illustrated at the lower portion of E in FIG. 10C is a special barcode attached on the back surface of rack 25 or the like, and indicates that "test tube is not set".

Test tube 6 (specimen container) is available in various sizes, and many types of caps 61 with different colors and shapes are used. Further, for test tube 6 set in the holder on the inner peripheral side of rack 25 and test tube 6 set in the holder on the outer peripheral side of rack 25, the way of imaging is different due to the difference in distance from imager 31 even if test tubes 6 are the same. As a result, there are variations in the captured images of test tubes 6. By using the features of the regions classified as A to E as described above, it is possible to easily discriminate whether cap 61 is mounted on test tube 6 for various images.

Summary of Features of Regions Classified as A to E

As described above, the features of the regions classified as A to E are summarized as follows.

A: A range in which background label 10 is imaged in a state with no obstruction (a region in which a pattern including a certain repeating pattern is imaged clearly in background label 10).

B: A range in which background label 10 is imaged through test tube 6 (a region in which a pattern including a certain repeating pattern of background label 10 imaged is distorted, the contrast of the pattern including the certain repeating pattern of background label 10 imaged is reduced, or the pattern including the certain repeating pattern of background label 10 imaged is partially hidden by refracted light or reflected light due to bending or refraction of the light passed through plastic or transparent glass of test tube 6).

C: A range in which background label 10 imaged is blocked by a label on which barcode 62 is printed (a region in which a pattern including a certain repeating pattern of background label 10 is completely blocked by a smooth label surface on which barcode 62 or characters are printed).

D: A range in which background label 10 imaged is blocked by cap 61 (a region in which a pattern including a certain repeating pattern of background label 10 imaged is completely blocked by cap 61).

E: A range in which background label 10 is not visible because background label 10 is outside the angle of view of imaging, and the inner surface of rack 25 is imaged as a dark space or a special barcode indicating that "test tube is not set" is imaged in the background (because background label 10 is outside the angle of view of imaging, a pattern including a certain repeating pattern of background label 10 is not imaged, and the inner surface of rack 25 is imaged as a dark space in the background or a small barcode is imaged in the background).

Cap 61 in D and the smooth label surface on which barcode 62 or characters are printed in C can be discriminated from each other based on whether characters or codes are printed, the texture or smoothness of the surface, and the difference in shape. Further, C and D can be discriminated based on whether a barcode is included in the region to be classified.

Note that when a pattern including a certain repeating pattern is used as the background by background label 10, the features of the image become easier to discriminate compared to when a plain background is used. In particular, it is possible to facilitate the discrimination of a space with no obstruction (a feature of a region classified into A), the bending or refraction of light (a feature of a region classified into B), and the blocking by a label or a cap (a feature of a region classified into C or D), which also making it possible to significantly improve the accuracy of the discrimination.

Flowchart of Detection Processing Using Image Recognition

As described above, controller 41 performs image recognition on the image acquired by camera section 3, and detects the presence or absence of test tube 6 cap 61 based on the features of each region recognized as A to E. The following sequentially describes these image recognition processing and detection processing.

Figure 12:
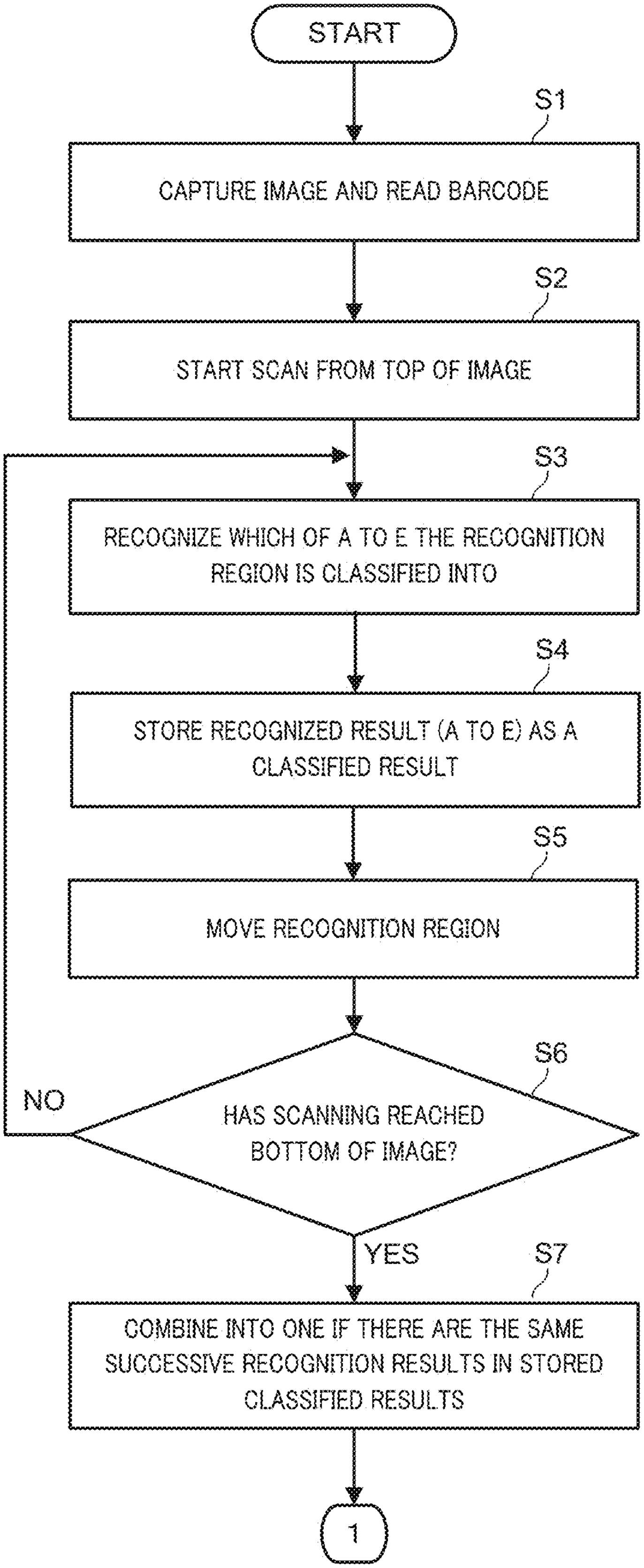
FIG. 12 is a diagram illustrating a flowchart of a detection processing using image recognition according to the embodiment of the present disclosure.
Figure 13:
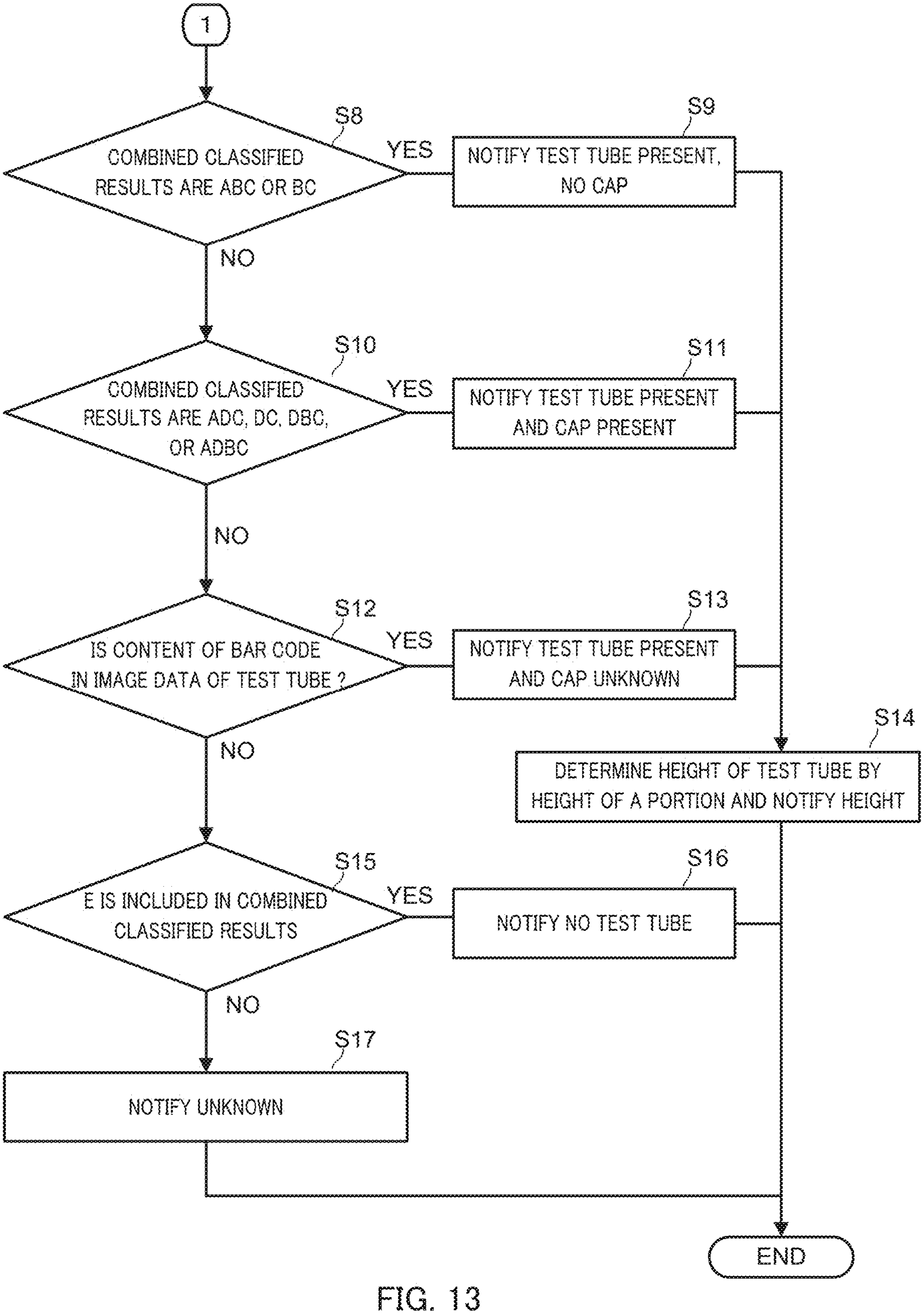
FIG. 13 is a diagram illustrating a flowchart of a detection processing using image recognition according to the embodiment of the present disclosure (continued from FIG. 12)

FIGS. 12 and 13 are flowcharts of the detection processing using image recognition executed by optical information reading apparatus 1. Optical information reading apparatus 1 executes the processing in the flowcharts illustrated in FIGS. 12 and 13 for each test tube 6 to be detected.

In S1 (Step 1), camera section 3 images test tube 6 as a detection target. Controller 41 reads (decodes) barcode 62 from the image data acquired by camera section 3.

In S2, controller 41 starts scanning from the top of the image data acquired by camera section 3 (see FIG. 10).

In S3, controller 41 executes image recognition processing on the recognition region of the image data and recognizes which of A to E the recognition region is classified into. The "recognition region" refers to a partial region of an image in which image recognition processing is performed in one scan.

In S4, controller 41 stores the recognized result (any of A to E) in storage section 42 as a classified result for each recognition region. The "classified results" refer to a set of recognition results for each recognition region.

In S5, controller 41 moves the recognition region of the image data to the next recognition region.

In S6, controller 41 determines whether the scanning has reached the bottom of the image data (whether the moved recognition region has reached the bottom portion of the image data).

In S6, when controller 41 determines that the scanning has reached the bottom of the image data (YES in S6), the flow proceeds to S7. In a case where controller 41 determines that the scanning is not performed to the bottom of the image data in S6 (NO in S6), the flow returns to S3, and the processing in S3 to S5 is continued.

In S7, controller 41 reads the stored classified results from storage section 42 and executes a process of combining the same recognition results into one when the same recognition results are continuous. For example, in a case where the image data is processed for each of a large number of recognition regions as illustrated in FIG. 10A, and the recognition results of the first to eleventh recognition regions are all A, the recognition results of the twelfth to twenty-second recognition regions are all B, and the recognition results of the twenty-third to fifty-first recognition regions are all C, controller 41 performs processing of combining the results of the first to eleventh recognition regions (classified results: AA . . . A) into one A, combining the results of the twelfth to twenty-second recognition regions (classified results: BB . . . B) into one B, and combining the results of the twenty-third to fifty-first recognition regions (classified results: CC . . . C) into one C. As a result of this processing, the combined classified results become ABC.

In S8, controller 41 determines whether the classified results combined in S7 are ABC or BC from the top.

In S8, when controller 41 determines that the classified results combined in S7 are ABC or BC from the top (YES in S8), the flow proceeds to S9. In S8, when controller 41 determines that the classified results combined in S7 are neither ABC nor BC from the top (NO in S8), the flow proceeds to S10.

In S9, controller 41 executes a processing of notifying "Test tube present, no cap". For example, controller 41 may execute a processing of notifying "Test tube present, no cap" by causing status LED 44 to light up in a predetermined manner by indicator control circuit 43, causing buzzer 52 to generate a predetermined notification sound, or transferring information to specimen testing apparatus 2 by communicator 51 and causing the display means of specimen testing apparatus 2 to display the information.

In S10, controller 41 determines whether the classified results combined in S7 are ADC, DC, DBC, or ADBC.

In S10, when controller 41 determines that the classified results combined in S7 are ADC, DC, DBC, or ADBC (YES in S10), the flow proceeds to S11. In a case where the controller 41 determines that the classified results combined in S7 are not any of ADC, DC, DBC, or ADBC (NO in S10), the flow proceeds to S12.

In S11, controller 41 executes a process of notifying "Test tube present, cap present". For example, controller 41 may execute a process of notifying "Test tube present, cap present" in the same manner as in S9.

In S12, controller 41 determines whether the content of barcode 62 read in S1 is data of test tube 6.

In S12, when controller 41 determines that the content of barcode 62 read in S1 is data of test tube 6 (YES in S12), the flow proceeds to S13. When controller 41 determines that the content of barcode 62 read in S1 is not data of test tube 6 (NO in S12), the flow proceeds to S15.

In S13, controller 41 executes a process of notifying "Test tube present, cap unknown". For example, controller 41 may execute a process of notifying "Test tube present, cap unknown" in the same manner as in S9.

In S14, controller 41 determines the height of test tube 6 based on the height of section A. The test tube 6 used as a specimen container has a height of 100 mm, 75 mm, or 66 mm, respectively, and the small container (test cup) has a height of 25 mm. Since the height of test tube 6 can be selected from a plurality of heights, it is possible to determine the height of the test tube by calculating the ratio of the recognition region occupied by the region classified as A with respect to the entire recognition region of a predetermined length.

In S15, controller 41 determines whether the classified results combined in S7 include E. At this time, it may be determined that the classified result of E is included in the image based on a fact that the content of barcode 62 read in S1 is a special barcode indicating that "test tube is not set".

In S15, when controller 41 determines that the classified results combined in S7 include E (YES in S15), the flow proceeds to S16. In S15, when controller 41 determines that the classified results combined in S7 do not include E (NO in S15), the flow proceeds to S17.

In S16, controller 41 executes a process of notifying "No test tube". For example, controller 41 may execute a process of notifying "No test tube" in the same manner as in S9.

In S17, controller 41 executes a process of notifying "Unknown". For example, controller 41 may execute a process of notifying "Unknown" in the same manner as in S9.

In S3, in the image recognition processing performed by controller 41, the manufacturer or user may preliminarily register multiple actual image data corresponding to each recognition result (any of A to E) at the time of apparatus manufacture or prior to use such that controller 41 compares the registered image data with the acquired image data so as to recognize the appearance of features (classified into any of A to E) from the image data. As the image recognition processing, a known method such as a pattern matching method, a method of comparing contrast, or a method using SSIM (Structural Similarity) may be used.

CMOS image sensor 312 used in imager 31 of optical information reading apparatus 1 of the present disclosure can execute the discrimination processing in the same manner regardless of whether it is a grayscale CMOS image sensor or a color CMOS image sensor. If the number of pixels is the same, a grayscale CMOS image sensor can provide higher resolution power than a color CMOS image sensor.

Optical information reading apparatus 1 of the present disclosure is an optical information reading apparatus provided with a function of detecting a cap in an apparatus that is widely used as a barcode reader. The barcode readers known in the related art are not limited to apparatuses installed in specimen testing apparatus 2, but are versatile apparatuses generally used in various situations for reading barcodes. As the barcode, in addition to a one-dimensional code, a two-dimensional code such as a stacked or matrix type two-dimensional code may be used. In addition, specific fonts and the like can also be read as well as barcodes.

Effects

According to optical information reading apparatus 1 of the present disclosure, it is possible to effectively prevent damage to probe 24 (suction tube) by detecting and notifying the user of a failure to remove cap 61 of test tube 6 (specimen container, reagent bottle). Further, according to optical information reading apparatus 1 of the present disclosure, by using a background pattern including a certain repeating pattern with background label 10, it is possible to facilitate discrimination through image recognition and to significantly improve the accuracy of the discrimination, which makes it possible to detect a failure to remove cap 61 of test tube 6 more easily and with higher accuracy. Further, optical information reading apparatus 1 of the present disclosure can easily implement a function of detecting a cap by changing only software without modifying hardware of an apparatus that is used as a barcode reader in the related art, and thus, has high versatility and is excellent in cost-effectiveness.

Modification Example 1

As the image recognition function of controller 41 included in processor 4 in the above-described embodiment, a trained machine learning model may be used. In this Modification Example 1, the trained machine learning model is configured to perform image recognition processing in optical information reading apparatus 1. The following describes Modification Example 1 using a trained machine learning model.

In a case where a trained machine learning model is used in the image recognition processing, it is essential that the machine learning model is trained by a manufacturer or a user during the manufacture of the apparatus or before use. Accordingly, the following will sequentially describe (1) learning processing of a machine learning model and (2) detection processing using a trained machine learning model.

(1) Learning Processing of Machine Learning Model

The following describes learning of the machine learning model.

A machine learning model is trained using an information processing apparatus. As the information processing apparatus, processor 4 of optical information reading apparatus 1 may be used, or a generally used computer may be used. In the learning processing, the learning of a machine learning model is performed by using learning data including image data for each recognition region and a result (any of A to E) recognized for each recognition region. The image data for each recognition region and the recognition result (any of A to E) for each recognition region may be obtained using the data obtained by the processing described in S1 to S6 of FIG. 12 described above. Through this learning processing, the machine learning model is trained to estimate the classified regions A to E to which the image data for each recognition region belong.

The machine learning model used here may be realized by any appropriate machine learning model, and for example, a machine learning model such as a known convolutional neural network may be used, or a known machine learning model (object detection library) such as YOLO may be used. In a case where YOLO is used, the detection result is a class and a bounding box (coordinates of the recognition region), and the learning is performed such that the output class is any one of the aforementioned A to E.

(2) Detection Processing Using Trained Machine Learning Model

The following describes detection processing using the trained machine learning model obtained as described above.

Flowchart of Detection Processing Using Trained Machine Learning Model

Figure 14:
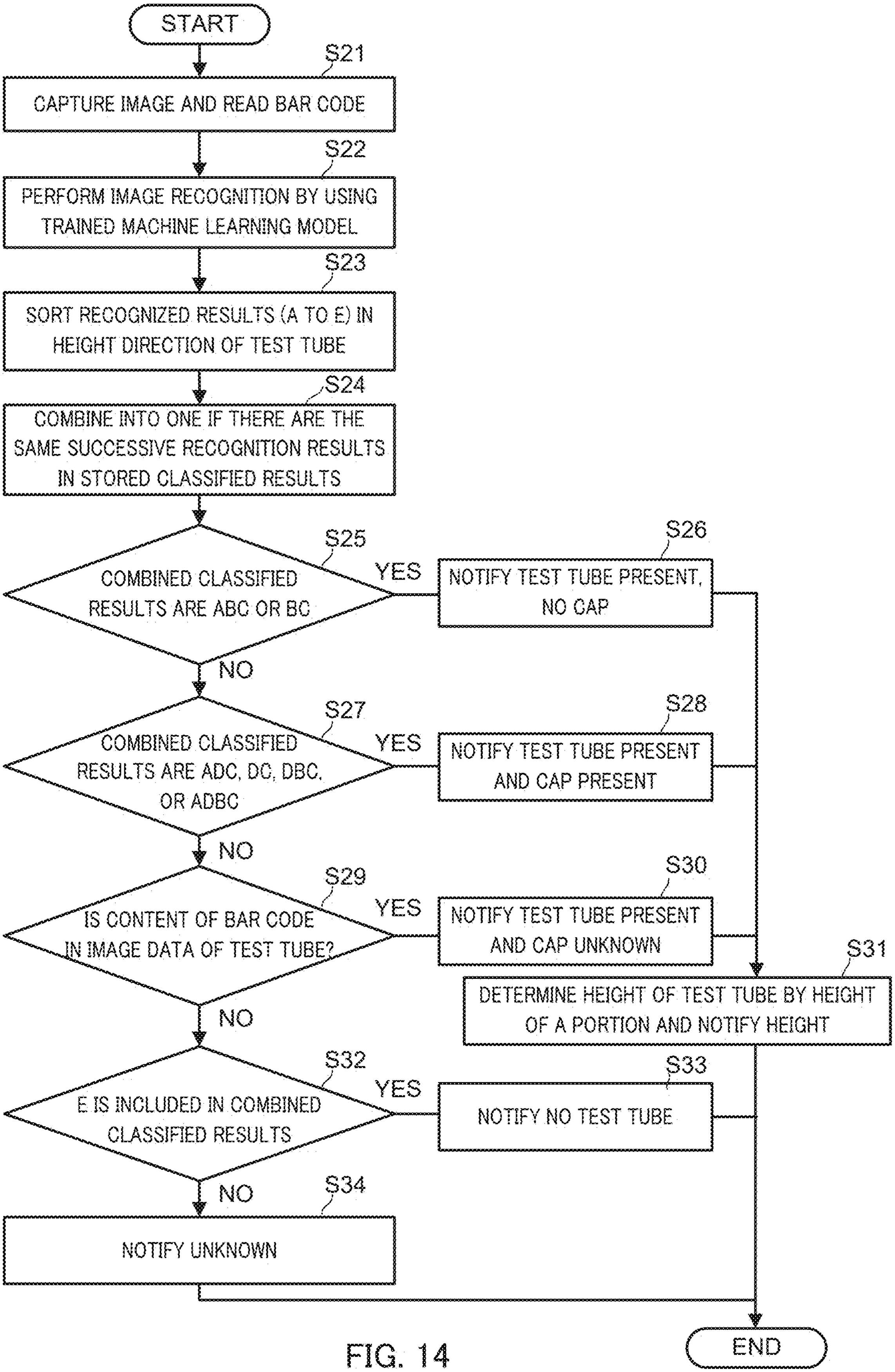
FIG. 14 is a diagram illustrating flowchart of a detection processing using a trained machine learning model according to the embodiment of the present disclosure.

Controller 41 activates the learned machine learning model by reading software for executing the trained machine learning model from storage section 42. FIG. 14 is a flowchart of a detection processing using a trained machine learning model executed by optical information reading apparatus 1. Controller 41 executes the processing illustrated in FIG. 14 for each test tube 6 to be detected.

In S21, camera section 3 images test tube 6 as a detection target. Controller 41 reads (decodes) barcode 62 from the image data acquired by camera section 3. The step is the same as S1 in FIG. 12 described above.

In S22, the trained machine learning model performs image recognition for each recognition region in the image data acquired by camera section 3, and recognizes the classified regions A to E to which the recognition regions belong.

In S23, controller 41 sorts the recognition results for each recognition region obtained by the trained machine learning model in the height direction of test tube 6.

In S24, when there are the same recognition results in a successive manner in a set (classified results) of recognition results sorted in the height direction of test tube 6, controller 41 executes a processing of combining the same recognition results into one. The combining is the same as S7 in FIG. 12 described above.

S25 to S34 executed by controller 41 may be executed in the same manner as S8 to S17 in FIG. 13 described above.

In a case where the image recognition processing is used, the identification depends on the position of the recognition region (as any of A to E), whereas in a case where the trained machine learning model is used, the image recognition and identification do not depend on the position of the recognition region (as any of A to E), and thus the identification rate can be increased as compared to a case where the image recognition processing is used.

Modification Example 2

Figure 15:
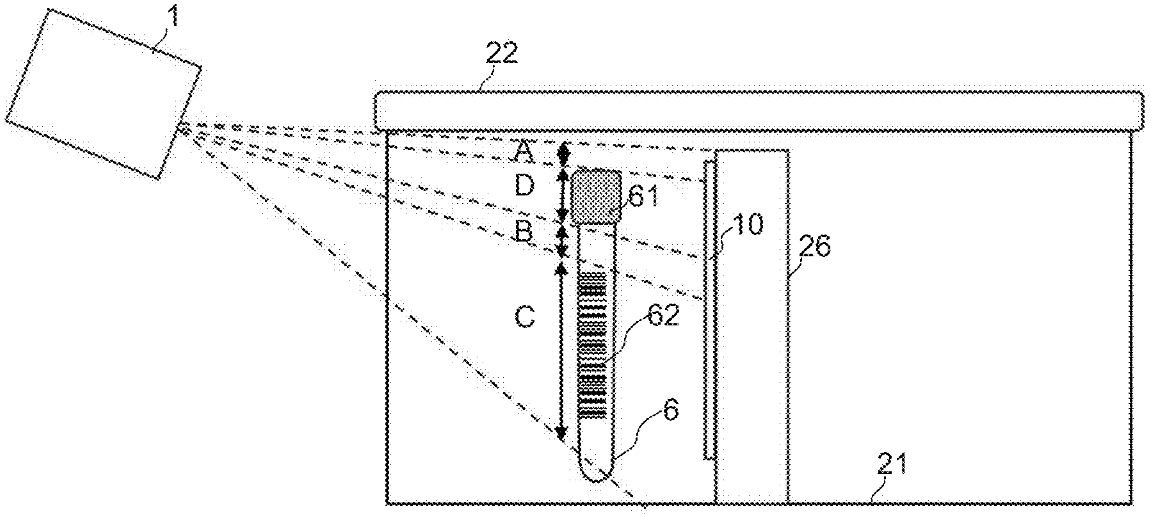
FIG. 15 is a diagram illustrating an example of imaging of a test tube using a background label by the optical information reading apparatus according to the embodiment of the present disclosure.

FIG. 15 is an example of imaging in a case where optical information reading apparatus 1 is installed in the specimen testing apparatus with the optical axis of imaging lens 311 directed downward, and background label 10 is attached to rotation shaft 26 of tub-shaped turntable container 21. Optical information reading apparatus 1 and background label 10 may be installed in such a manner. With this installation, the upper side of test tube 6 is clearly imaged.

Modification Example 3

Figure 16:
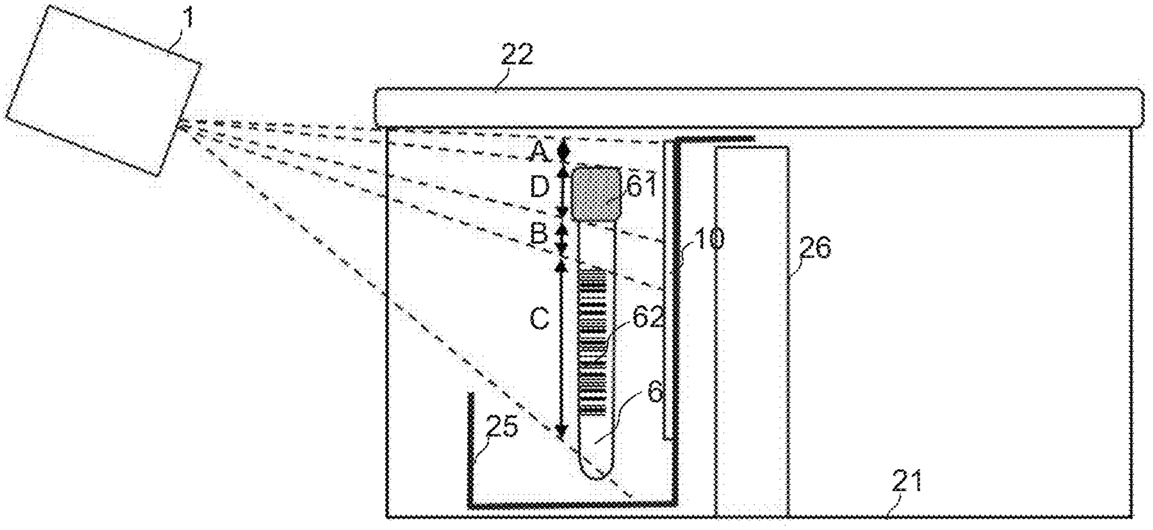
FIG. 16 is a diagram illustrating an example of imaging of a test tube using a background label by the optical information reading apparatus according to the embodiment of the present disclosure.

FIG. 16 is an example of imaging in a case where optical information reading apparatus 1 is installed in the specimen testing apparatus with the optical axis of imaging lens 311 directed downward, and background label 10 is attached to the back surface of rack 25 of tub-shaped turntable container 21. Optical information reading apparatus 1 and background label 10 may be installed in such a manner. With this installation, the upper side of test tube 6 is clearly imaged, and the pattern of background label 10 is also clearly imaged.

Modification Example 4

As described in the section of Background Label, a background label on which a checkerboard pattern as illustrated in FIG. 8A is printed is used, but a pattern including a certain repeating pattern as illustrated in FIGS. 8B to 8F may be used as the background label, for example. The pattern including a certain repeating pattern may be any pattern, and is not limited to those illustrated in FIGS. 8B to 8F.

Further, a pattern that characteristically changes depending on the location (FIGS. 8G and 8H) may be used. For example, the pattern of the background label that is larger on the side farther from imager 31 and is smaller on the side closer to imager 31 may be adopted so that the size of the pattern recognized by imager 31 is constant regardless of the distance.

Figure 8H:
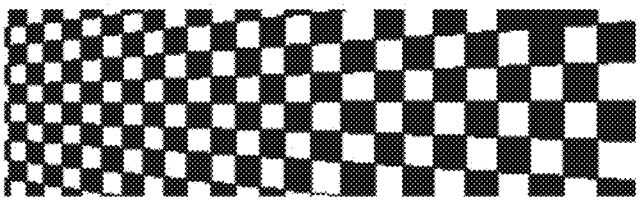
FIGS. 8A to 8H are diagrams illustrating examples of background labels according to the embodiment of the present disclosure.
Figure 8G:
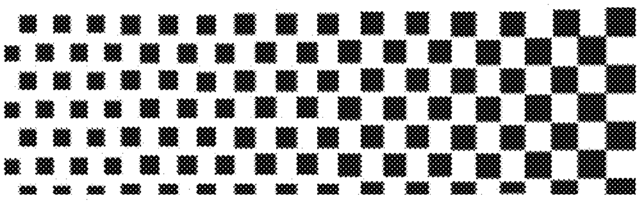
Figure 8F:
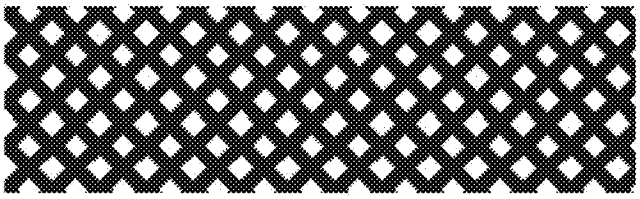
Figure 8E:
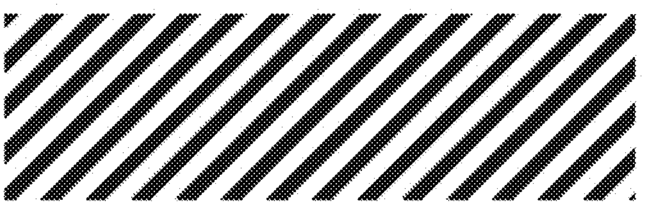
Figure 8D:
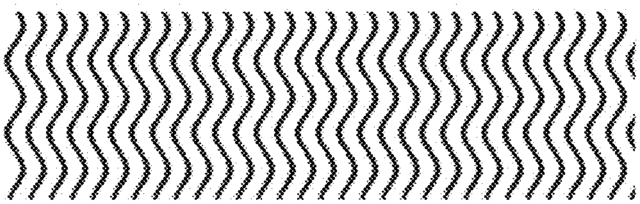
Figure 8C:
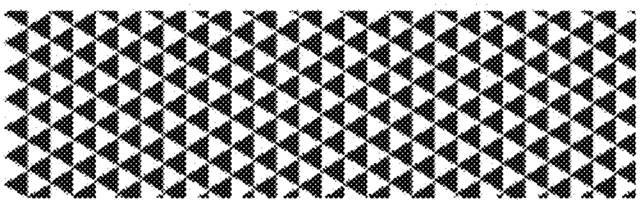
Figure 8B:
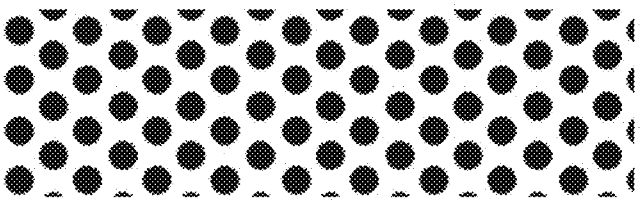
Figure 8A:
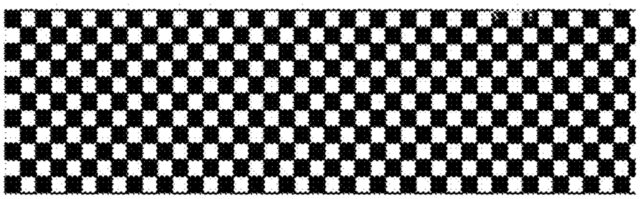

The pattern that characteristically changes depending on the location may be any pattern as long as the pattern can be said to be a pattern that characteristically changes depending on the location, such as a pattern whose concentration, density, size, or the like continuously changes, or a pattern that continuously or stepwisely changes to constitute a gradation as a whole, and is not limited to those illustrated in FIGS. 8G and 8H.

The above description of the embodiments is with reference to the drawings, but the present disclosure is not limited to such examples. It is clear that those skilled in the art can conceive of various examples of changes or modifications within the scope of the claims. It is understood that such changes or modifications also fall within the technical scope of the present disclosure. In addition, each component of the embodiment may be arbitrarily combined to the extent that the intent of the present disclosure is not departed from.

In the above-mentioned embodiments, the notation " . . . part" used for each component may be replaced by other notations such as " . . . circuitry," " . . . assembly," " . . . device," " . . . unit," or " . . . module. Calculation may be read as calculation.

This disclosure may be realized in software, hardware, or software in conjunction with hardware. Each functional block used in the description of the above embodiments may be partially or entirely realized as an LSI, an integrated circuit, and each process described in the above embodiments may be partially or entirely controlled by a single LSI or a combination of LSIs. The LSI may be composed of individual chips or may be composed of a single chip to include some or all of the functional blocks. The LSI may have data inputs and outputs. LSIs may be referred to as ICs, system LSIs, super LSIs, or ultra LSIs, depending on the degree of integration.

The method of integrated circuitry is not limited to LSIs, but may be realized with dedicated circuits, general-purpose processors or dedicated processors. Field Programmable Gate Array (FPGA), which can be programmed after LSI manufacturing, and reconfigurable processors, which can reconfigure the connections and settings of circuit cells inside the LSI, may also be used. This disclosure may be realized as digital or analog processing.

Furthermore, if a technology for integrated circuits replacing LSI appears due to advances in semiconductor technology or another derived technology, the technology may naturally be used to integrate functional blocks. The application of biotechnology, etc. may be a possibility.

INDUSTRIAL APPLICABILITY

The present disclosure is effective, for example, in detecting the presence or absence of a cap in a container containing a specimen or a reagent.

REFERENCE SIGNS LIST

1 Optical information reading apparatus
2 Specimen testing apparatus (biochemical automatic analysis apparatus)
3 Camera section
4 Processor
5 Sub-board
6 Test tube
10 Background label
21 Tub-shaped turntable container
22 Lid of turntable container
23 Dispenser
24 Probe (suction tube)
25 Rack
26 Rotation shaft
31 Imager
311 Imaging lens
312 CMOS image sensor
32 Controller (MCU)
33 LED lighting drive circuit
34 LED light
41 Controller (CPU)
42 Storage section (main storage section, auxiliary storage section)
43 Indicator control circuit
44 Status LED
51 Communicator
52 Buzzer
61 Cap
62 Barcode
63 Specimen

What is claimed is:

1. An optical information reading apparatus comprising:
an imager that acquires an image by imaging a container to which a code is attached and a pattern including a certain repeating pattern or a pattern whose density or size changes arranged in a background of the container; and
a controller that decodes the code from the image and detects presence or absence of a cap of the container based on a state of the pattern in the image.

2. The optical information reading apparatus according to claim 1,
wherein the controller classifies a region of the image for each region based on the state of the pattern, and detects presence or absence of the cap of the container by classified results that are plurality of combinations of the classified regions.

3. The optical information reading apparatus according to claim 2, wherein the classified region is any one of:
a first region that is imaged in a state in which the pattern is clear;
a second region that is imaged in a state in which the pattern is distorted, contrast is reduced, or the pattern is hidden by refracted light or reflected light;
a third region that is imaged in a state in which the pattern is not imaged due to a label surface on which the code or a character is printed;
a fourth region that is imaged in a state in which the pattern is not imaged due to the cap; and
a fifth region in which the background is imaged and the pattern is not imaged because the pattern is located outside an angle of view.

4. The optical information reading apparatus according to claim 3,
wherein the controller detects that the cap of the container is present when the fourth region is included in the classified results, the fourth region is located at the beginning of the classified results or is located below the first region, and the fourth region is located above the second region or the third region.

5. An optical information reading method, comprising: by an optical information reading apparatus,
acquiring an image by imaging a container to which a code is attached and a pattern including a certain repeating pattern or a pattern whose density or size changes arranged in a background of the container;
decoding the code from the image; and
detecting presence or absence of a cap of the container based on a state of the pattern in the image.

6. An optical information reading program causing an optical information reading apparatus to execute:
acquiring an image by imaging a container to which a code is attached and a pattern including a certain repeating pattern or a pattern whose density or size changes arranged in a background of the container;

decoding the code from the image; and detecting presence or absence of a cap of the container based on a state of the pattern in the image.

* * * * *